United States Patent
Liu et al.

(10) Patent No.: US 11,058,636 B2
(45) Date of Patent: Jul. 13, 2021

(54) DISPERSION PROCESS OF ADAPALENE IN A GEL PREPARATION

(71) Applicant: ZHAOKE (GUANGZHOU) OPHTHALMIC DRUG COMPANY LIMITED, Guangzhou (CN)

(72) Inventors: Jing Liu, Hefei (CN); Gang Li, Hefei (CN); Xiaoyi Li, Hong Kong (HK); Xiangrong Dai, Hefei (CN); Lei Yin, Hefei (CN); Juan Ling, Hefei (CN)

(73) Assignee: ZHAOKE (GUANGZHOU) OPHTHALMIC DRUG COMPANY LIMITED, Guangzhou (CN)

( * ) Notice: Subject to any disclaimer, the term of this patent is extended or adjusted under 35 U.S.C. 154(b) by 175 days.

(21) Appl. No.: 16/228,808

(22) Filed: Dec. 21, 2018

(65) Prior Publication Data

US 2019/0192431 A1    Jun. 27, 2019

(30) Foreign Application Priority Data

Dec. 21, 2017    (CN) .......................... 201711392438.9

(51) Int. Cl.
*A61K 9/10*        (2006.01)
*A61K 47/10*       (2017.01)
(Continued)

(52) U.S. Cl.
CPC .............. *A61K 9/10* (2013.01); *A61K 9/0014* (2013.01); *A61K 9/06* (2013.01); *A61K 31/192* (2013.01); *A61K 31/7056* (2013.01); *A61K 47/10* (2013.01); *A61K 47/12* (2013.01); *A61K 47/14* (2013.01); *A61K 47/32* (2013.01); *A61K 47/34* (2013.01); *A61P 17/10* (2018.01); *B01F 3/0811* (2013.01); *B01F 3/1214* (2013.01); *B01F 3/2071* (2013.01); *B01F 2003/0846* (2013.01); *B01F 2003/1257* (2013.01); *B01F 2215/0032* (2013.01)

(58) Field of Classification Search
CPC .......... A61P 37/08; A61P 31/00; A61P 37/04; A61P 11/02; A61P 11/06; A61P 37/00; A61P 11/04; A61P 17/00; A61P 17/04; A61P 43/00; A61P 17/16; A61P 27/02; A61P 27/14; A61P 31/04; A61P 31/14; A61P 33/00; A61P 37/02; A61P 39/02; C12N 15/117; C12N 2310/17; C12N 2310/315; C12N 2310/333; C12N 2310/336; C12N 2310/335; C12N 2320/35; C12N 2730/10134; C12N 2795/18123; C07H 21/00; C07H 21/02; C07H 21/04; A61K 39/0011; A61K 39/39; A61K 45/06; A61K 2039/55561; A61K 2039/57; A61K 8/042; A61K 2039/545; A61K 2800/48; A61K 2800/548; A61K 31/7088; A61K 39/12; A61K 39/35; A61K 39/36; A61K 8/06; A61K 8/365; A61K 8/8152; A61K 8/91; A61K 2039/5258; A61K 2039/543; A61K 2039/55555; A61K 2039/55566; A61K 2039/70; A61K 2800/594; A61K 39/0291; A61K 39/07; A61K 39/08; A61K 39/292; A61K 47/10; A61K 47/22; A61K 47/26; A61K 47/6901; A61K 47/6931; A61K 49/0004; A61K 49/0093; A61K 49/0097; A61K 8/35; A61K 8/37; A61K 8/73; A61K 8/737; A61K 8/891; A61K 9/0043; A61K 9/0095; A61K 9/107; A61K 9/1075; A61K 9/1652; A61K 9/205; A61K 9/5026; A61K 9/5036; A61K 9/5073; A61Q 19/00; A61Q 19/10; A61Q 5/06; A61Q 17/04; A61Q 5/006; A61Q 5/02; A61Q 5/12; A61Q 15/00; A61Q 5/004; A61Q 11/00; A61Q 1/02; A61Q 1/12; A61Q 5/00; C08L 2666/02; C08L 5/00; C08L 5/14; A01K 2207/10; A01K 2227/105; A01K 2267/0387; A01K 67/027

See application file for complete search history.

(56) References Cited

FOREIGN PATENT DOCUMENTS

CN    1989956 A      7/2007
CN    101485675   *  1/2008   ......... A61K 31/7056
(Continued)

OTHER PUBLICATIONS

CN101485675, Li et al, translation (Year: 2008).*
CN102274159, Chen et al., translation. (Year: 2011).*

*Primary Examiner* — Audrea B Coniglio
*Assistant Examiner* — Audrea Buckley
(74) *Attorney, Agent, or Firm* — Bayramoglu Law Offices LLC

(57) ABSTRACT

A dispersion process of adapalene gel preparation, including the following steps: pulverizing adapalene raw material to D50 not more than 10 μm and D90 not more than 30 μm by dry detection; adding methyl p-hydroxybenzoate, 1,2-propanediol, carbomer 980 and disodium edetate in water, heating and stirring consistently to obtain a matrix in a uniform jelly; adding poloxamer 188, propylene glycol and ethylene glycol phenyl ether in water, stirring and heating to prepare a mixed solution; adding adapalene in the mixed solution prepared, emulsifying at a high speed, then adding to the matrix for thorough stirring; and then adding a triethanolamine aqueous solution for homogenization and stirring. The preparation prepared has good emulsifying and dispersing effect of adapalene, can be expanded on a large scale, and the industrial promotion prospect is good.

7 Claims, No Drawings

(51) Int. Cl.
  *A61K 31/192* (2006.01)
  *A61K 47/34* (2017.01)
  *A61P 17/10* (2006.01)
  *A61K 47/14* (2017.01)
  *A61K 9/00* (2006.01)
  *A61K 31/7056* (2006.01)
  *A61K 9/06* (2006.01)
  *A61K 47/12* (2006.01)
  *A61K 47/32* (2006.01)
  *B01F 3/08* (2006.01)
  *B01F 3/12* (2006.01)
  *B01F 3/20* (2006.01)

(56) References Cited

FOREIGN PATENT DOCUMENTS

| | | | | |
|---|---|---|---|---|
| CN | 102274159 | * | 7/2011 | ............... A61K 9/00 |
| CN | 103099775 A | | 5/2013 | |
| CN | 103417473 A | | 12/2013 | |
| CN | 103462882 A | | 12/2013 | |
| CN | 105411999 A | | 3/2016 | |

* cited by examiner

DISPERSION PROCESS OF ADAPALENE IN A GEL PREPARATION

CROSS REFERENCE TO THE RELATED APPLICATIONS

This application is based upon and claims priority to Chinese Patent Application No. 201711392438.9, filed on Dec. 21, 2017, the entire contents of which are incorporated herein by reference.

TECHNICAL FIELD

The invention relates to the field of medicine, in particular to a dispersion process of adapalene in a gel preparation.

BACKGROUND

Adalalene is a white or off-white powder chemical, with a chemical name 6-[3-(1-adamantyl)-4-methoxyphenyl]-2-naphthoic acid, molecular formula C28H28O3, molecular weight 412.52000, which is insoluble in water or ethanol, slightly soluble in tetrahydrofuran. Adapalene is a dermatological drug that is clinically suitable for the treatment of acne vulgaris, which is mainly characterized by acne, papules and pustules. It can also be used to treat acne on the face, chest and back.

Adapalene mainly binds to RARPβ and RARγ, and has weak binding to RARα. It inhibits glutamine invertase of keratinocytes in vitro, inhibits the keratinization process, and regulates cell differentiation. Animal experiments have found that adapalene has acne dissolution and local anti-inflammatory effects, and its anti-inflammatory activity may be related to its interference with the function of polymorphonuclear leukocytes and the metabolism of arachidonic acid.

Adapalene is poorly soluble, so adapalene is present in suspension in aqueous gels. For suspension gels, the pharmacopoeia has strict requirements. The Appendix 0114 Gel Particle Size in 2015 edition of the Pharmacopoeia requires: no particles more than 180 μm should be detected for the suspension gel. Therefore, the size of adapalene drug substance plays a crucial role in the absorption of this product. The particle size relates to the homogeneity of the formulation, bioavailability, formulation stability, and the like. None of the relevant patents and literatures that have been published places studies in detail on the particle size of adapalene. For a gelling preparation, the emulsification and dispersion process is also very important, which directly determines the quality of the preparation. Current patent documents are as follows:

CN201510809500.4, titled "a method for preparing adapalene gel"

CN201310393546.3 titled "an adapalene gel and a preparation method thereof"

CN201310350418.0 titled "an adapalene gel and a preparation method thereof"

CN201210378524.5 titled "adapalene gel"

CN200510135286.5 titled "an adapalene gel composition and a preparation method thereof"

These patents specify that the formulation has a particle size of less than 50 μm, but does not systematically study the particle size of adapalene, crushing process and the detailed particle size distribution. Moreover, the disclosed dispersion processes of the above patent documents are all stirring process in small-scale, the batch size is small, and all the preparations are emulsified and dispersed after the formulation is finished. Because of large volume of the preparation which needs emulsification and dispersion, the emulsifying and dispersing effect is not good, resulting in poor uniformity and poor appearance of the preparation, thus, the uniformity and stability of the preparation can not be guaranteed under the particle size. Because the preparation which needs to be emulsified and dispersed is bulky, the emulsification and dispersion effect is not good, resulting in poor uniformity and poor appearance of the preparation, thereby the uniformity and stability of the preparation produced under such particle size cannot be guaranteed.

SUMMARY

It is an object of the present invention to provide a dispersion process for a gel formulation of adapalene comprising the following steps:

Step 1: pulverizing adapalin raw material until D50 under dry detection not more than 10 um and D90 under dry detection not more than 30 um;

Step 2: adding methyl p-hydroxybenzoate, 1,2-propanediol, carbomer 980, disodium edetate in water, heating and stirring persistently to obtain a matrix in a uniform jelly;

Step 3: adding poloxamer 188, propylene glycol, ethylene glycol phenyl ether in water, stirring and heating to prepare a mixed solution;

Step 4: adding adapalene to the mixed solution prepared in step 3; after high-speed emulsification adding to the matrix and stirring well; then adding triethanolamine aqueous solution to homogenize and stir.

Preferably, in step 1, the adapalene starting material is pulverized using a jet mill. More preferably, the crushing parameters are a venturi-tube pressure of 8.0-11.0 bar, an annular pressure of 8.0-10.0 bar, and a feed rate of 50-150 rpm.

Preferably, the heating in steps 2 and 3 means heating to 50-60° C.

Preferably, the mass ratio of water, methylparaben, 1,2-propanediol, carbomer 980, and disodium edetate in step 2 is 480:2-4:80-100:5-7:1-2.

Preferably, the mass ratio of water to poloxamer 188, propylene glycol, ethylene glycol phenyl ether in step 3 is 1:30-40:1.

Preferably, the mass ratio of adapalene to the mixed solution in step 4 is 1:20-200.

More preferably, the emulsification in step 4 is emulsified at a speed of 12-20 m/s for 20-40 min.

Preferably, the method of the invention further comprises a sterilization treatment step.

More preferably, the sterilization treatment is moist heat sterilization at 121° C.

The inventor of the present invention conducted a comprehensive scientific study on the particle size control and emulsification dispersion process of adapalene, and solved the problem of emulsification dispersion and reasonable particle size control of adapalene gel preparation. In specific embodiments, the test result of the adapalene compound gel prepared by the dispersion process of the invention shows that the particle size requirement is met: D90≤50 um; the content uniformity requirement: China Pharmacopoeia 2015 stipulating that A+2.2S<15. The emulsification and dispersing effect of adapalene in the preparation prepared by the process of the invention is good, and the process can be expanded on a large scale, and the industrial promotion prospect is good.

DETAILED DESCRIPTION

The present invention discloses a dispersion process of adapalene in a gel preparation, and those skilled in the art can learn from the contents herein and appropriately improve the process parameters. It is to be understood that all such alternatives and modifications are apparent to those skilled in the art and are considered to be included in the present invention. The processes of the present invention have been described in terms of the preferred embodiments, and it is apparent that those skilled in the art can change and adapt and combine the methods and applications described herein to implement and apply the present invention without departing from the contents, spirits and scope of the invention.

In order to make those skilled in the art better understand the technical solutions of the present invention, the present invention will be further described in detail below with reference to specific embodiments.

Example 1: Dispersion Process of Adapalene

1. Pulverization and Particle Size Control of Adapalene Raw Material
(1) Pulverization of Adapalene Raw Materials
Method: The adapalene was pulverized using a jet mill to achieve the target particle size.
Pulverization parameters: venturi-tube pressure 8.0 bar, annular pressure 8.0 bar, feed rate 50 rpm
(2) Particle Size Control:
Method: Taking the appropriate amount of this product, using Malvern MS3000 laser particle size analyzer, dry detection, D50 should not greater than 10 μm, D90 should not greater than 30 um.
2. Dispersing Process of Adapalene
(1) Matrix Preparation
60 Kg purified water was added to the emulsifying tank and heated to 55±5° C. Homogenization and stirring was started, then 250 g methyl parahydroxybenzoate and 10 kg 1, 2-propanediol were added and stirred homogeneously for 10 min, then 700 g carbomer 980, 125 g ethylenediamine tetraacetic acid disodium were added and stirred homogeneously for 20 minutes. A uniform gelatinized matrix was obtained.
(2) Solution Preparation
1) 5 Kg purified water was added into the mixing tank, stirring was started and 1.125 Kg triethanolamine was added;
2) 5 Kg purified water was added to the tank, stirring was started, and 200 g Poloxamer 188 was added to the tank, heating to 55±5° C. was started, stirred for 15 minutes, and 6 kg 1,2 propanediol and 200 g ethylene glycol phenyl ether were added and stirred for 5 min.
(3) Sterilization
The matrix, triethanolamine aqueous solution, Poloxamol 188 aqueous solution, 1,2-propanediol and ethylene glycol phenyl ether mixture were sterilized under moisture heating at 121° C. for 20 minutes.
(4) Preparation Process
1) Clindamycin hydrochloride was dissolved in 7 Kg purified water to prepare clindamycin hydrochloride solution, after aseptic filtration, the solution was added directly to the matrix and mixed well.
2) 125 g adapalene was added to a sterilized mixture solution of 2.5 Kg 1, 2-propanediol, ethylene glycol phenyl ether and Poloxamer 188 mixture, high speed emulsification (speed 15 m/s) and dispersion was carried out for 30 mins in the emulsifying tank, then added into the matrix to stir, then triethanolamine aqueous solution was added slowly to the emulsifying tank, and was stirred homogeneously for 20 minutes.
3) Bubbles were removed in vacuum. Samples were taken and the viscosity, pH, the content of clindamycin hydrochloride, and the content and uniformity of adapalene were measured.

Example 2

1. Pulverization and Particle Size Control of Adapalene Raw Material
(1) Pulverization of Adapalene Raw Materials
Method: The adapalene was pulverized using a jet mill to achieve the target particle size.
Pulverization parameters: venturi-tube pressure 9.0 bar, annular pressure 9.0 bar, feed rate 100 rpm
(2) Particle Size Control:
Method: Taking the appropriate amount of this product, using Malvern MS3000 laser particle size analyzer, dry detection, D50 should not greater than 10 μm, D90 should not greater than 30 um.
2. Dispersing Process of Adapalene
(1) Matrix Preparation
60 Kg purified water was added to the emulsifying tank and heated to 55±5° C. Homogenization and stirring was started, then 500 g methyl parahydroxybenzoate and 12 kg 1,2-propanediol were added and stirred homogeneously for 10 min, then 750 g carbomer 980, 200 g ethylenediamine tetraacetic acid disodium were added and stirred homogeneously for 20 minutes. A uniform gelatinized matrix was obtained.
(2) Solution Preparation
1) 5.5 Kg purified water was added into the mixing tank, stirring was started and 1.125 Kg triethanolamine was added;
2) 5 Kg purified water was added to the tank, stirring was started, and 500 g Poloxamer 188 was added to the tank, heating to 55±5° C. was started, stirred for 15 minutes, and 15 kg 1,2 propanediol and 500 g ethylene glycol phenyl ether were added and stirred for 5 min.
(3) Sterilization
The matrix, triethanolamine aqueous solution, Poloxamol 188 aqueous solution, 1,2-propanediol and ethylene glycol phenyl ether mixture were sterilized under moisture heating at 121° C. for 20 minutes.
(4) Preparation Process
1) Clindamycin hydrochloride was dissolved in 7 Kg purified water to prepare clindamycin hydrochloride solution, after aseptic filtration, the solution was added directly to the matrix and mixed well.
2) 125 g adapalene was added to a sterilized mixture solution of 5 Kg 1,2-propanediol, ethylene glycol phenyl ether and Poloxamer 188 mixture, high speed emulsification (speed 15 m/s) and dispersion was carried out for 30 mins in the emulsifying tank, then added into the matrix to stir, then triethanolamine aqueous solution was added slowly to the emulsifying tank, and was stirred homogeneously for 20 minutes.
3) Bubbles were removed in vacuum. Samples were taken and the viscosity, pH, the content of clindamycin hydrochloride, and the content and uniformity of adapalene were measured.

Example 3

(1) The Pulverization:
After pulverization the raw materials of adapalene was subjected to dry method detection and D50 was found not more than 10 um, D90 was found not more than 30 um. Adapalene was pulverized using a jet mill to achieve the target particle size.
Pulverization parameters: Venturi-tube pressure 10.0 bar, annular pressure 9.0 bar, feed speed 100 rpm.
(2) Matrix Preparation:
Methyl parahydroxybenzoate and 1,2-propanediol were added into purified water, stirred evenly and heated continuously. Carbomer 980 and disodium ethylenediamine tetraacetic acid were added and stirred to form a uniform gelatinized matrix;
Specifically, 60 Kg purified water was added to the emulsifying tank and heated to 55±5° C. After homogenization and stirring were started, 250 g methyl parahydroxybenzoate and 10 kg 1,2-propanediol were added, then 750 g carbomer 980 and 125 g ethylenediamine tetraacetic acid disodium was added, stirred homogeneously for 20 minutes, to form a uniform gelatinized matrix.
(3) Solution Preparation:
Poloxamer 188, propanediol and ethylene glycol phenyl ether were added into purified water, stirred and heated for 5 min. 5 Kg purified water was added to the tank, stirring was started, and 500 g Poloxamer 188 was added, heating was started to 55±5° C., stirred for 15 minutes, 15 kg 1,2-propanediol and 500 g ethylene glycol phenyl ether were added and stirred.

(4) Dispersion Steps:
Adapalene was added to a mixture solution of 1,2-propanediol, ethylene glycol phenyl ether and Poloxamer 188, after high speed emulsification, added the matrix to stir fully; then triethanolamine aqueous solution was added and stirred homogeneously. In the emulsifying tank, high speed emulsification (15 m/s) (12~20 m/s) was performed to disperse for 30 min (20~40 min), then added the matrix and stirred evenly, triethanolamine aqueous solution was slowly added into the emulsifying tank, and stirred homogeneously for 20 minutes.
Clindamycin hydrochloride solution can be optionally added to prepare clindamycin hydrochloride adapalene compound gel.
5) Bubbles were removed in vacuum. Samples were taken and the viscosity, pH, the content of clindamycin hydrochloride, and the content and uniformity of adapalene were measured.

Example 4

The results of adapalene hydrochloride clindamycin compound gel prepared from examples 1-3 are as follows:
1. Uniformity of the Preparation

| Batch number | pH | viscosity (mP·s) | particle size (D90) | clindamycin hydrochloride content (%) | adapalene content | uniformity (%) |
|---|---|---|---|---|---|---|
| 20150511 | 6.82 | 5680 | 17.5 um | 99.79 | 101.20% | A + 2.2S = 2.11 |
| 20150513 | 6.84 | 5570 | 16.7 um | 98.76 | 103.91% | A + 2.2S = 7.69 |
| 20150515 | 6.88 | 5870 | 17.0 um | 102.86 | 102.73% | A + 2.2S = 6.11 |

Note:
particle size requirements: D90 ≤ 50 um;
Content uniformity requirement: According to China Pharmacopoeia 2015, A + 2.2S < 15 is in accordance with the provisions.
detection method of particle size of the preparation: 5-10 g of the product was taken and mixed with 25 ml water. The saturated solution of adalalene in Tween-80 was used as the dispersing medium, the rotational speed was 1500 rpm, and the ultrasonic intensity was 20%.

2. Stability of the Preparation

| batch no. | time (months) | appearance | pH value | viscosity (mP·s) | total impurity in adapalene (%) | total impurity in clindamycin (%) | adalalene content (%) | clindamycin content (%) |
|---|---|---|---|---|---|---|---|---|
| 20150511 | 0 | milky white gel | 6.82 | 5680 | 0.34 | 1.18 | 101.20 | 99.79 |
| | 3 | milky white gel | 6.84 | 5650 | 0.40 | 1.36 | 99.83 | 99.22 |
| | 6 | milky white gel | 6.98 | 5612 | 0.43 | 1.60 | 99.35 | 98.78 |
| | 9 | milky white gel | 6.82 | 5633 | 0.35 | 1.80 | 99.68 | 98.58 |
| | 12 | milky white gel | 6.74 | 5590 | 0.38 | 2.02 | 99.70 | 98.41 |
| | 18 | milky white gel | 6.80 | 5566 | 0.40 | 2.21 | 99.47 | 98.18 |
| | 24 | milky white gel | 6.88 | 5525 | 0.44 | 2.46 | 99.23 | 98.30 |
| 20150513 | 0 | milky white gel | 6.84 | 5570 | 0.32 | 1.28 | 103.91 | 98.76 |
| | 3 | milky white gel | 6.84 | 5618 | 0.38 | 1.38 | 103.22 | 98.65 |
| | 6 | milky white gel | 6.80 | 5590 | 0.40 | 1.64 | 102.98 | 98.50 |
| | 9 | milky white gel | 6.78 | 5532 | 0.38 | 1.82 | 102.90 | 98.54 |
| | 12 | milky white gel | 6.79 | 5450 | 0.44 | 2.10 | 102.98 | 98.32 |
| | 18 | milky white gel | 6.83 | 5440 | 0.42 | 2.21 | 102.87 | 98.04 |
| | 24 | milky white gel | 6.88 | 5323 | 0.42 | 2.40 | 102.89 | 97.77 |
| 20150515 | 0 | milky white gel | 6.88 | 5870 | 0.35 | 1.22 | 102.73 | 102.86 |
| | 3 | milky white gel | 6.80 | 5830 | 0.40 | 1.34 | 102.44 | 102.54 |
| | 6 | milky white gel | 6.83 | 5805 | 0.41 | 1.55 | 102.56 | 102.20 |
| | 9 | milky white gel | 6.80 | 5780 | 0.38 | 1.75 | 102.54 | 101.90 |
| | 12 | milky white gel | 6.84 | 5800 | 0.44 | 1.98 | 102.21 | 101.56 |
| | 18 | milky white gel | 6.80 | 5735 | 0.41 | 2.22 | 102.45 | 101.53 |
| | 24 | milky white gel | 6.85 | 5700 | 0.40 | 2.39 | 102.2 | 101.22 |

According to the above data, it can be known that the uniformity and stability of the prepared preparations 20150511, 20150513 and 20150515 are good. Compared with 0-month sample, no significant change was found for the long-term 24-month sample with respect to all test indicators.

3. Pharmacokinetics and Clinical Study of the Preparation

Efficacy and safety assessments were performed through human pharmacokinetics studies and clinical studies. The results of clinical trials show that the safety of the product is good, and it has remarkable curative effect on acne vulgaris.

The above description only shows preferred embodiment of the present invention, and it should be noted that those skilled in the art can also make a number of improvements and modifications without departing from the principles of the present invention, and these improvements and modifications should be considered falling within the scope of protection of the present invention.

What is claimed is:

1. A method for preparing a dispersed adapalene gel formulation, comprising the following steps:
    step 1: pulverizing adapalene raw material to D50 not more than 10 um and D90 not more than 30 um by dry detection, wherein a jet mill is used to pulverize adapalene starting material and the pulverization parameters include a venturi-tube pressure of 8.0-11.0 bar, an annular pressure of 8.0-10.0 bar, and a feed rate of 50-150 rpm;
    step 2: adding methyl p-hydroxybenzoate, 1,2-propanediol, carbomer 980 and disodium edetate in water, heating and stirring consistently to obtain a matrix in a uniform jelly;
    step 3: adding poloxamer 188, propylene glycol and ethylene glycol phenyl ether in water, stirring and heating to prepare a mixed solution, wherein, a mass ratio of water and poloxamer 188, propylene glycol, and ethylene glycol phenyl ether is 1:30-40:1;
    step 4: adding adapalene in the mixed solution prepared in step 3, emulsifying at a high speed, then adding to the matrix obtained in step 2 for thorough stirring; and then adding a triethanolamine aqueous solution for homogenization and stirring.

2. The method according to claim 1, wherein, the heating in steps 2 and 3 is performed up to 50-60° C.

3. The method according to claim 1, wherein, a mass ratio of the water, methyl p-hydroxybenzoate, 1,2-propanediol, carbomer 980, and disodium edetate in step 2 is 480:2-4:80-100:5-7:1-2.

4. The method according to claim 1, wherein, in step 4 a mass ratio of adapalene to the mixed solution obtained in step 2 is 1:20-200.

5. The method according to claim 1, wherein, the emulsification in step 4 is performed at a speed of 12-20 meters per second for 20-40 minutes.

6. The method according to claim 1, further comprising a sterilization step.

7. The method according to claim 6, wherein, the sterilization is a moist heat sterilization at 121° C.

* * * * *